United States Patent [19]

Johnson

[11] Patent Number: 4,614,429
[45] Date of Patent: Sep. 30, 1986

[54] ATMOSPHERIC CONTRAST TRANSMITTANCE MONITOR

[75] Inventor: Richard W. Johnson, San Diego, Calif.

[73] Assignee: The United States of America as represented by the Secretary of the Air Force, Washington, D.C.

[21] Appl. No.: 610,142

[22] Filed: May 14, 1984

[51] Int. Cl.[4] ............................................. G01N 21/47
[52] U.S. Cl. .................................... 356/343; 356/222
[58] Field of Search ............... 356/222, 338, 339, 340, 356/341, 342, 343

[56] References Cited

U.S. PATENT DOCUMENTS

| | | | |
|---|---|---|---|
| 2,198,971 | 4/1940 | Neufeld | 88/23 |
| 2,907,889 | 10/1959 | Nichols et al. | 356/342 |
| 3,572,949 | 3/1971 | Rouet | 356/206 |
| 3,606,564 | 9/1971 | Lisark | 356/103 |
| 3,619,624 | 11/1971 | Sorenson | 250/218 |
| 3,672,775 | 6/1972 | Fruengel | 356/339 X |
| 3,724,951 | 4/1973 | Seelbinder | 356/102 |
| 4,111,559 | 9/1978 | Smith et al. | 356/201 |
| 4,200,398 | 4/1980 | Persson et al. | 356/437 |
| 4,403,862 | 9/1983 | Lofgren et al. | 356/437 |
| 4,475,816 | 10/1984 | Mooradian et al. | 356/338 X |

OTHER PUBLICATIONS

"Scattering Functions of Light in the Atmospheric Boundary", by O. D. Barteneva, Bull. Acad. Sci., USSR Geophysics Series, pp. 1237–1244 (1960).
"Airborne Measurements of Optical Atmospheric Properties in Northern Germany", S. Q. Duntley et al., AFGL-TR-76-0188 (1976).
"Airborne Measurements of Optical Atmospheric Properties, Summary and Review III", S. Q. Duntley, AFGL-TR-78-0286 (1978).
"Daytime Visibility and Nephelometer Measurements related to Its Determination", R. W. Johnson, Atmos. Eniro, vol. 15, No. 10/11, pp. 1835–1845 (1981).
"Measurements of Optical Atmospheric Quantities in Europe and Their Application to Modelling Visible Spectrum Contrast Transmittance", R. W. Johnson, AGARD-CP-300.
"An Experimental Device for Real Time Determination of Slant Path Atmospheric Contrast Transmittance", R. W. Johnson, AFGL-TR-82-0125.
"An Experimental Device for Real Time Determination of Slant Path Atmospheric Contrast Transmittance", R. W. Johnson, AFGL-TR-83-0053.

Primary Examiner—Davis L. Willis
Assistant Examiner—Matthew W. Koren
Attorney, Agent, or Firm—Donald J. Singer; Bobby D. Scearce

[57] ABSTRACT

An atmospheric contrast transmittance monitor is described which comprises an electro-optical system including three solid state transducer assemblies interfaced with a small dedicated microprocessor for control of the system in either semi-automatic or operator interactive modes for real-time monitoring of the optical state of the atmosphere, one assembly comprising a compact multi-channel nephelometer of novel configuration for providing directional volume scattering function measurements on atmospheric samples, and a pair of staring fisheye lens scanners and associated detectors for scanning the upper and lower hemisphere radiance distributions. The system requires only a few hundred watts of input power and is less than one meter in length overall, and, operating in pulsed mode, has been used to measure the scattering characteristics of clear-day room air, with adequate sensitivity to suggest the capability of measurements approaching $10^{-5} m^{-1}$, i.e., sea level molecular.

6 Claims, 4 Drawing Figures

ATMOSPHERIC CONTRAST TRANSMITTANCE MONITOR

RIGHTS OF THE GOVERNMENT

The invention described herein may be manufactured and used by or for the Government of the United States for all governmental purposes without the payment of any royalty.

BACKGROUND OF THE INVENTION

The invention relates generally to the on-line use of combined nephelometric and directional sky radiance systems in a novel electro-optical device for real time monitoring of the optical state of the atmosphere.

As the deployment of tactically oriented electro-optical systems becomes increasingly commonplace, there is a continuing and concomittant requirement for understanding those environmental factors most influencing their performance. In many cases, it is the influence of poor weather conditions upon visible and infrared transmittance that is a primary factor in degrading the performance of the electro-optical systems.

The primary data base upon which many visible spectrum atmospheric models have been built consists mainly of selected profile measurements of volume scattering coefficients and $4\pi$ radiance distributions. The C-130 class nephelometer (see Johnson et al, "Measurements of Optical Atmospheric Quantities in Europe and Their Application to Modelling Visible Spectrum Contrast Transmittance", Proceedings of the AGARD 29th Symposium of the Electromagnetic Wave Propagation Panel on Special Topics in Optical Propagation, Vol. AGARD-CP-300, pp 14-1 to 14-12 (1981); and Johnson, "Daytime Visibility and Nephelometer Measurements Related to its Determination", Atmospheric Environment, Vol 15, No 10/11 pp 1835-1845 (1981)) measured both the total volume scattering coefficient, and the directional scattering function at 30° and 150°. Although this data base has provided a substantial quantity of excellent quality data for both general modelling and specific slant path contract transmittance determinations, its acquisition and manipulation have been expensive and time consuming operations. A compact, reliable, and simple electro optical system that would provide additional directional scattering and sky radiance data is required.

The airborne instrument system of the present invention fulfills the foregoing described need by providing a novel airborne instrument system for providing real-time outputs of atmospheric directional contrast transmittance values utilizing a simplified computational procedure. The system of the invention provides an output which is the slant path contrast transmittance along any preselected path of sight within the sampled environment. The invention is primarily intended for airborne application within the lower troposphere, but is easily adaptable for static ground based application in the determination of surface directional visibilities. The system of the invention provides the needed atmospheric transmittance information to support a broad variety of activities related to military tactical operations, meteorological forecasting procedures and fundamental research into the optical properties of the atmosphere.

It is, therefore, a principal object of the present invention to provide an improved atmospheric contrast transmittance monitor.

It is a further object of the invention to provide a novel airborne system for providing real time outputs of directional atmospheric contrast transmittance functions.

It is yet another object of the invention to provide a novel contrast transmittance monitor for providing directional scattering data uniquely appropriate for this application.

These and other objects of the present invention will become apparent as the detailed description of certain representative embodiments thereof proceeds.

SUMMARY OF THE INVENTION

In accordance with the foregoing principles and objects of the present invention, a novel atmospheric contrast transmittance monitor is described which comprises an electro-optical system including three solid state transducer assemblies interfaced with a small dedicated microprocessor for control of the system in either semi-automatic or operator interactive modes for real-time monitoring of the optical state of the atmosphere, one assembly comprising a compact, multi-channel nephelometer of novel configuration for providing directional volume scattering function measurements on atmospheric samples, and a pair of staring fisheye lens scanners and associated detectors for scanning, respectively, the upper and lower hemisphere radiance distributions. The system requires only a few hundred watts of input power and is less than one meter in length overall, and, operating in pulsed mode, has been used to measure the scattering characteristics of clear-day room air, with adequate sensitivity to suggest the capability of measurements approaching $10^{-5}$ m$^{-1}$, i.e., sea level molecular.

DESCRIPTION OF THE DRAWINGS

The present invention will be more clearly understood from the following detailed description of certain representative embodiments thereof read in conjunction with the accompanying drawings wherein.

DETAILED DESCRIPTION

Mathematical Analysis

Figure 1:
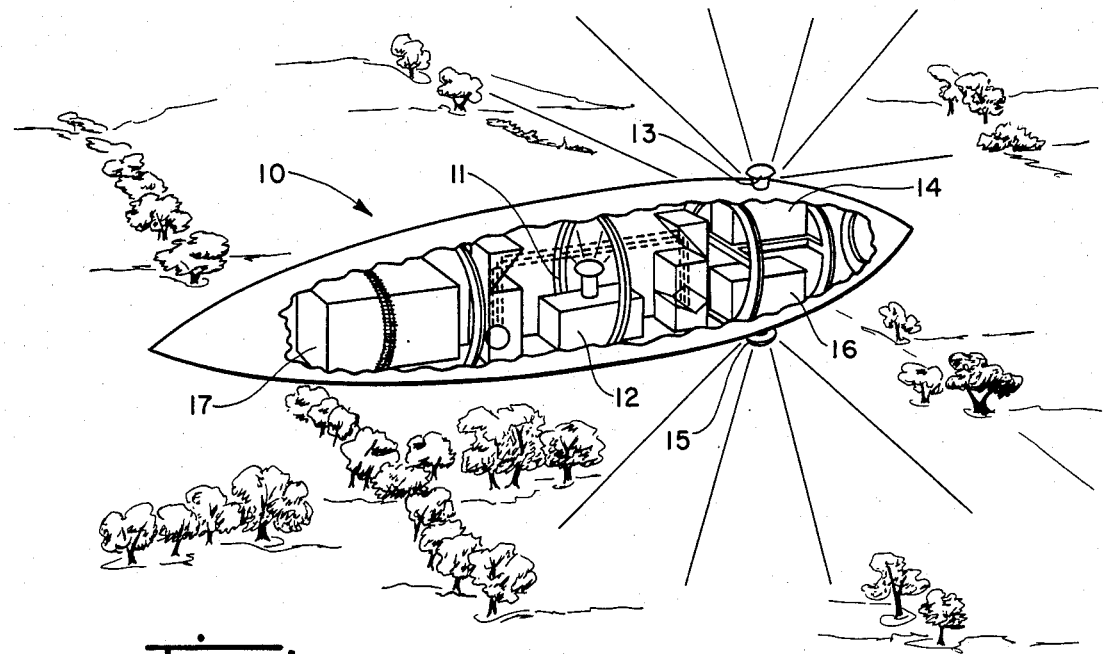
FIG. 1 is a simplified cutaway view of the system of the present invention schematically illustrating the major components thereof.

In order to calculate visual spectrum contrast transmittance along any path of sight, one needs a reasonably complete specification of the $4\pi$ radiance distribution which surrounds the path of sight, and a specification of the volume scattering function that is representative of the aerosol along the path of sight. When these data are available, then the computational chain yielding directional path reflectance or its equivalent can be structured to readily match the measurement characteristics of the electro optical system. The basic relationship for the equilibrium radiance $L_q$ may be given (after Duntley, et al, "Airborne Measurements of Optical Atmospheric Properties in Northern Germany", University of California, San Diego, Scripps Institution of Oceanography Visibility Laboratory, AFGL-TR-76-0188 (1976)) by the following:

$$L_q(z,\theta,\phi) = {}_s\epsilon(z)[\sigma(z,\beta)/s(z)] + \int_{4\pi} L(z,\theta',\phi')[\sigma(z,\beta')/s(z)]d\Omega \quad (1)$$

where ${}_s\epsilon(z)$ is the scalar irradiance of the sun (or full moon), $\beta$ is the angle between the sun and the path of sight, $L(z,\theta',\phi')$ is the apparent radiance of the sky or ground for direction $\theta'$ and $\phi'$, $\sigma$ is the volume scattering function, and $s(z)$ is the volume scattering coefficient over the spherical range of observation $\Omega$. $\beta'$ is the angle between the path of sight at $\theta,\phi$ and the radiance at $\theta',\phi'$, and is found by the relationship, $$\cos\beta' = \sin\theta\sin\phi\sin\theta'\sin\phi' + \sin\theta\cos\phi\sin\theta'\cos\phi' + \cos\theta\cos\theta'$$

which may be simplified to, $$\cos\beta' = \sin\theta\sin\theta'\cos(\phi-\phi') + \cos\theta\cos\theta' \quad (2)$$

The ratio $\sigma(z,\beta)/s(z)$ is the proportional directional volume scattering function at angle $\beta$ and altitude z. When the sky is fully overcast, the first term on the right side of equation (1) is negligible.

It is the scalar irradiance which designates the flux that enters into the computations of equilibrium radiance and path function when the directional radiances are not known or used. It is the directionality of that flux combined with the directionality of the proportional directional volume scattering function which produces the unique equilibrium radiance associated with each path of sight.

The solution (integration) of equation (1) may be simplified severely without inducing significant error on the resulting values of $L_q$ (see Duntley et al, "Airborne Measurements of Optical Atmospheric Properties, Summary and Review III", University of California, San Diego, Scripps Institution of Oceanography Visibility Laboratory, AFGL-TR-78-0286 (1978)). This feature is important to establishing the utility of the novel monitoring system herein described. Calculations indicate that each of the upper and lower hemispheres of observation as seen by the system may be divided, for computational purposes, into as few as 8 special zones whose average radiances, when substituted into the integral, will yield the same results to within ±10%.

The proportional directional scattering function $\sigma(z,\beta)/s(z)$ that is required for use within equation (1) has traditionally come from measurements made by an airborne integrating nephelometer, and selections from Barteneva's catalog ("Scattering Functions of Light in the Atmospheric Boundary Layer", Bull Acad Sci, USSR Geophysics Series, 1237–1244 (1960)). However, a specification of total volume scattering coefficient is sufficient to specify an appropriate volume scattering function from Barteneva; thus defining the necessary directionalities of any sample aerosol.

A system which will provide both the $4\pi$ radiance distributions and the directional scattering functions required by equation (1), will yield the additional desired atmospheric properties according to the following computations.

First, the point function equilibrium radiance $L_q(z,\theta,\phi)$ may be calculated from equation (1) and the path function L* may be calculated from, $$L^*(z,\theta,\phi) = L_q(z,\theta,\phi)s(z) \quad (3)$$

Path radiance is then given as, $$L^*(z,\theta,\phi) = \Sigma_i L^*(z,\theta,\phi)T_{ri}\Delta r \quad (4)$$

and directional path reflectance $R_r^*$ may be calculated from, $$R_r^*(z,\theta,\phi) = \frac{\pi L_r^*(z,\theta,\phi)}{E(z,d)T_r(z,\theta,\phi)} \quad (5)$$

where $E(z,d)$ is the downdwelling radiance calculated from, $$E(z,d) = {}_s\epsilon(z)\cos\theta_s + \int_{2\pi} L(z,\theta',\phi')\cos\theta'd\Omega \quad (6)$$

where $\theta_s$ is the sun zenith angle. Contrast transmittance $T_r$ is therefore given by $$T_r(z,\theta,\phi) = [1 + R_r^*(z,\theta,\phi)/{}_bR_o(z_t,\theta,\phi)]^{-1} \quad (7)$$

It should be noted that at each stage of the computation, each of the inputs required by equations (1) through (7) can be provided by the output from either the $4\pi$ radiance measurement or the scattering function measurement. If the airborne system's repetition rate is adequate, measurements and calculations can be made at sufficiently short altitude increments to preclude the need for interpolation.

System Description

Referring now to FIG. 1, shown therein is a simplified cutaway view of the monitor system 10 of the present invention which may be attached to an aircraft for performance of the intended function. The monitor system 10 comprises a three-part electro optical solid state transducer system interfaced with a built-in microprocessor, and includes a compact multi-channel nephelometer 11 and associated radiation detector system 12. The system comprising compact nephelometer system 11 and detector system 12 provides directional volume scattering function measurements in form similar to but more extensive than that provided by the C-130 integrating nephelometer system referred to previously. A first fisheye scanning lens 13 scans the upper hemisphere radiance distribution and feeds a specialized image plane detector array 14 described in more detail below. Similarly, fisheye lens 15 feeding an associated detector array system 16 provide lower hemisphere radiance distributions. Electronics 17 including microcomputer controls and a power supply may be miniaturized to provide a compact, self contained system.

A variety of electro-optical devices exist for the measurement of energy scattered from an illuminated volume of aerosol and which are calibrated in terms of visibility. In all of these devices, the relationship, $$s(z) = \int_{4\pi} \sigma(z,\beta)d\Omega \quad (8)$$

is utilized to calculate total scattering.

Figure 2:
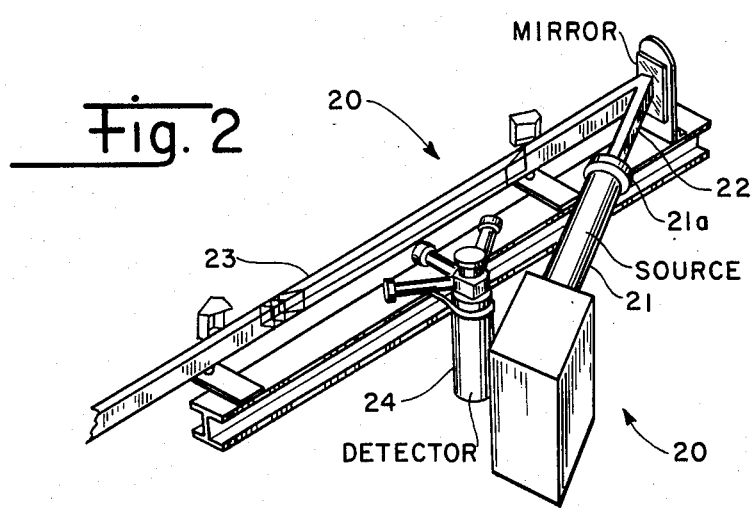
FIG. 2 is an illustration of a conventional nephelometer.

The most reliable method for providing a measurement of the scattered energy utilizes the nephelometer 20 depicted in FIG. 2, which is illustrative of the C-130 (see Johnson et al, supra). The optical system of nephelometer 20 utilizes a light source 21 providing a cylindrically limited projector beam stopped at 21a to provide a beam 22 of rectangular cross section which provides good geometrical definition of an illuminated scattering volume 23. A shielded irradiometer head 24 performs the integration of equation (8) over scattering angles between 5° and 172°. The detector assembly's secondary optical channels measure relatively narrow angle, i.e., 2° field of view, directional scattering at both 30° and 150° which allows the determination of a forward to backward scattering ratio that can be used to characterize the sample aerosol volume 23.

The nephelometer 20 as illustrated in FIG. 2 performs reliably and consistently when properly aspirated, but has two major drawbacks to miniaturization and increased directional scattering function measurement: first, the existing nephelometer 20 utilizes photomultiplier detection, which is bulkily configured precluding efficient expansion of its optical configuration, in need of relatively complex regulated high voltage circuitry; and second, the existing nephelometer system 20 is designed to operate within several moderately narrow spectral bands within the visible spectrum over an altitude range of 0–6 km and thus employs a 500 watt xenon short arc projection system as a flux source, which requires large amounts of electrical power supplied on a continuous basis, and thus is inappropriate for the low power requirement satisfied by the present invention.

Figure 3:
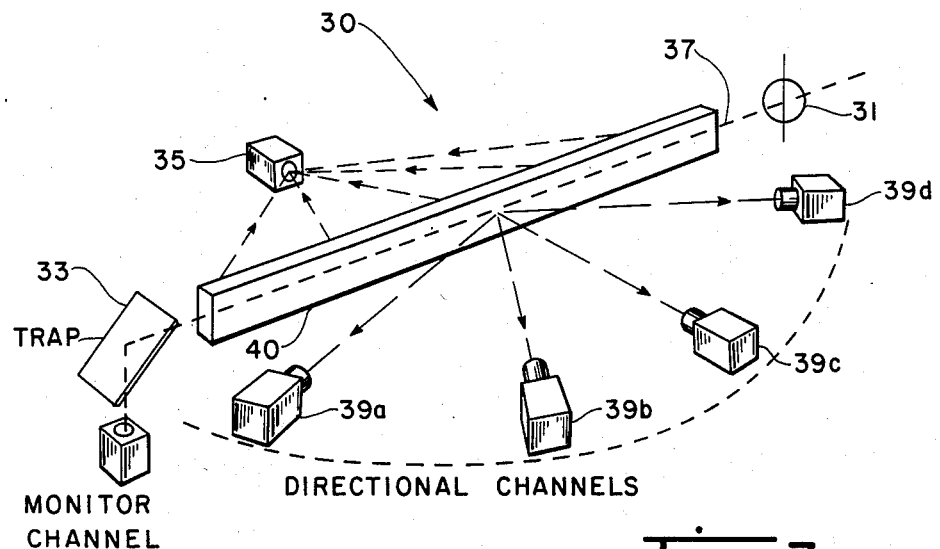
FIG. 3 is a schematic of the improved nephelometer system of the present invention.

Referring now to FIG. 3, shown therein is a schematic of the compact nephelometer of the present invention including legends defining the basic geometric relationships most useful in its operation. The system 30 of the invention is desirably compact, and the full scale distance between source 31 and trap 33 is approximately 21 centimeters. Unlike nephelometer 20 of FIG. 2 discussed above, the integrator channel 35 of system 30 is located on the opposite side of the flux beam 37 from the directional collection detectors 39 a–d, which configuration is necessary for overall compactness.

Source 31 is comprised of an illuminator and a compact projector for illuminating a sample aerosol volume 40. The illuminator has been built in two configurations to demonstrate the invention.

In the first configuration, the illuminator is a small 75 watt xenon short arc lamp powered through a specially designed current modulator circuit characterized by approximately 10:1 current modulation above the minimum simmer current required to keep the lamp ignited, and by circuit parameters selected to drive the lamp at approximately 150 cycles per second with an average duty cycle of ten percent. In a representative unit built in demonstration of the invention, a type X75-2002 lamp (Illumination Industries, Inc.) was used, although other lamps may be suitable.

In the second configuration the illuminator is a small pulsed lamp system which uses an EG&G model FX-131 bulb type xenon flash tube at a rated maximum energy per flash of 200 joules and an average power of up to 100 watts. The use of short duration high energy pulses is a desirable attribute, in that it aids substantially in reducing the overall size and power consumption of the system.

The existing nephelometer 20 (see FIG. 2) generated an illuminated sample volume of approximately 4815 cm$^3$ (viz., $5 \times 9 \times 107$ cm). In the present invention, however, it is highly desirable to provide a substantially reduced volume 40 size of about 42 cm$^3$ (viz., $0.7 \times 2.8 \times 21.5$ cm). A rectangle-rectangle intercept between the receiver and projector optics is used whereby substantially the entire width of the projector beam may be captured by the receiver optics.

The increase in both optical efficiency and projected beam energy from system 30 over that of the previous system was substantial, enabling the use of commercially available photodiode detectors 39a–d of FIG. 3 (e.g., EG&G HUV-4000B or HUV-1000B; Silicon Detector Corp. SCD-444-42-12-261; or United Detector Technology PIN 10AP).

The function of the multi-channel nephelometer 30 is to provide measurements identifying the magnitude of the volume scattering coefficient s(z) and the shape of the volume scattering function $\sigma(z,\beta)$. The original C-130 nephelometer measured s(z) and $\sigma(z,\beta)$ at 30° and 150°, whereas the system 30 of FIG. 3 provides measurements of $\sigma(z,\beta)$ at four angles, viz., 15°, 55°, 100° and 140°, to enhance the reliability of the characterization of the sample aerosol.

Several informational redundancies which uniquely characterize this device, are available from the four selected angular measurements, particularly when combined with the fifth measurement, that of total volume scattering coefficient s(z). The apparent ability for the prediction of $\sigma(z,\beta)$ from a knowledge of s(z) alone presents a strong experimental diagnostic for the reliability of the measurements defining the two sides of equation (8). The relationship between the forward scatter at 15° and the minimum or backscatter at 100° or 140° is adequate to recreate a close approximation of the total phase function (volume scattering function) and thus cross-check the simultaneous measurement of s(z). The measurements of the directional scattering in the vicinity of 55° is relatively unaffected by the shape of the phase function, and driven for the most part then by the aerosol concentration alone, thus providing an independent datum for an additional determination of s(z). When the experimental measurements are conducted in increasingly heavy fog and cloud conditions, the transition from haze is markedly identified by the relationship between the directional scattering in the backscatter directions. The ratio between the 10° and 140° scattering should readily identify the regime inhabited by large spherical water drops from that of the drier, more irregular haze aerosols.

Figure 4:
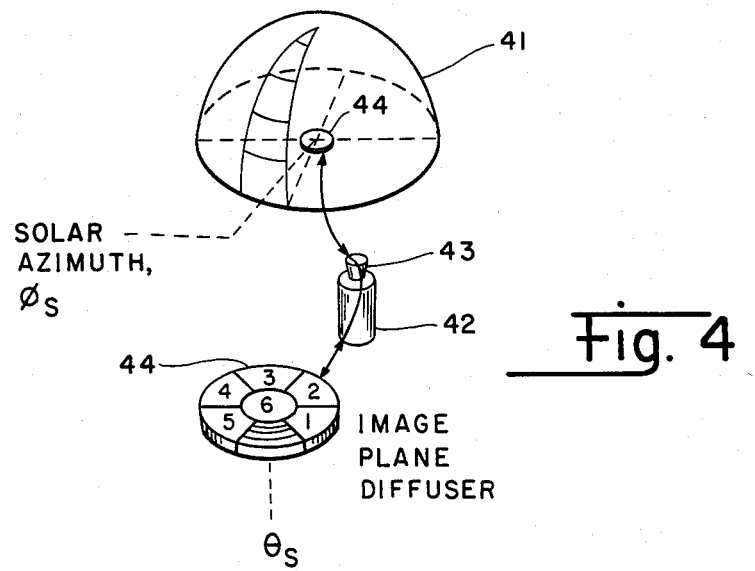
FIG. 4 is a schematic of a fisheye scanner and image plane diffuser system of the present invention useful for radiance distribution measurements.

The proposed configuration for the scanner (13 and 15 of FIG. 1) and associated detector arrays (14 and 16) are illustrated in FIG. 4. The observed scene is illustrated as the sample hemisphere 41. The fisheye scanner 42 observes this hemisphere through its 180° field of view fisheye lens 43 and images the hemispheric radiance distribution at its image plane. At the system's image plane is a segmented, diffusely transmitting disc 44 of the same diameter as the image of the observed hemisphere. It is this image plane diffuser 44 that divides the observed scene (hemisphere 41) into a selection of zones and performs the optical integration that allows the detection of each zone's average radiance. The configuration illustrated in FIG. 4 implies an individual detector behind each zone in the diffuser 44, i.e., behind each of the six numbered zones shown in FIG. 4, plus four behind the smaller unnumbered zones. It is the radiometric measurement made by these detectors which provides the radiance values used in the solution of the equations (1) through (7).

The zone arrangement illustrated in FIG. 4 is only one of many possible configurations useful for determining the solid angles of integration of equation (1) (or more accurately, the summation which approximates equation (1)), so long as the selected configuration defines and isolates each of the zones which most significantly contribute to the upper hemisphere's radiant directionality. In particular, the zones which will contain the image of the solar disc and aureole must be carefully specified.

The detector system 16 (FIG. 1) may be substantially identical to detector 14; however, because of the minimal directional effects from typical terrains seen in the lower hemisphere, detector system 16 may be configured more simply with fewer detector zones than that desired for detector 14.

The lens selected for successful demonstration of the invention was the Soligor fisheye conversion lens, a 180° adapter lens designed for use with a broad variety of prime lenses yielding, in each particular combination, a resultant focal length of 0.15 times the prime focal length. Thus, a standard 50 mm focal length is, with the adapter, converted to 7.5 mm. The essential feature is that the flux bundle emerging from the exit pupil of the adapter lens is highly collimated and about 10 mm in diameter. Thus, a broad variety of secondary lenses can be readily located within this flux bundle to alter the resultant image diameter, and also allow space for the insertion of additional optical elements.

The HUV-4000B detector was used in the demonstration system with each of the scanner's large zones and the HUV-1000B was chosen for each of the smaller zones associated with the solar azimuth (see FIG. 4 where $\phi_s$=solar azimuth).

Several operational evaluations were conducted to demonstrate the utility of the invention. The demonstration system 10 (FIG. 1) was used on both clear and overcast days, in orientations which measured the average radiance as detected in both the larger sky zones and the smaller sun zones. The observed flux levels are more than adequate for detection by the system.

The present invention, as hereinabove described, provides a novel atmospheric contrast transmittance monitor system for real time monitoring of the optical state of the atmosphere. It is understood that certain modifications to the invention as described may be made, as might occur to one with skill in the field of this invention, within the scope of the appended claims. Therefore, all embodiments contemplated hereunder which achieve the objects of the invention have not been shown in complete detail. Other embodiments may be developed without departing from the spirit of this invention or from the scope of the appended claims.

I claim:

1. An electro-optical system for monitoring the optical state of the atmosphere, comprising:
   a. a nephelometer system for measuring directional volume scattering functions on atmospheric samples, said nephelometer system including means for controllably illuminating a predetermined atmospheric sample volume, and a plurality of radiation detectors for measuring the illumination scattered by said sample volume at a preselected plurality of scattering angles and yielding a corresponding preselected plurality of specifications of aerosol characteristics of said atmospheric sample volume, and for providing output signals corresponding to said plurality of specifications;
   b. first and second scanning lenses for scanning, respectively, upper and lower radiance distributions of the atmosphere from respective upper and lower hemispheres of observation;
   c. first and second detector means, operatively connected to respective said first and second scanning lenses for detecting the radiance observed by the scanning lenses and for providing output signals corresponding to the intensities of the observed said radiance distributions; and
   d. electronic means, operatively connected to said plurality of radiation detectors and to said first and second detector means and responsive to the output signals from said radiation detectors and said first and second detector means, for calculating atmospheric contrast transmittance according to a preprogrammed computational procedure.

2. The system as recited in claim 1 wherein said scanning lenses comprise 180° staring fisheye lenses.

3. The system as recited in claim 1 wherein said first and second detector means include segmented radiation diffuser plate means for separately measuring radiation distribution observed by said lenses at separate respective spherical segments of said respective upper and lower hemispheres of observation.

4. The system as recited in claim 1 wherein said radiation detectors comprise photodiode detectors.

5. The system as recited in claim 1 comprising four said radiation detectors disposed about said atmospheric sample volume for measuring the illumination scattered by said volume at scattering angles of 15°, 55°, 100°, and 140°, respectively.

6. The system as recited in claim 1 wherein said illuminating means comprises a xenon flash tube.

* * * * *